(12) United States Patent
Yang et al.

(10) Patent No.: US 8,541,652 B2
(45) Date of Patent: Sep. 24, 2013

(54) **MUTANTS OF PHA SYNTHASE FROM *PSEUDOMONAS* SP. 6-19 AND METHOD FOR PREPARING LACTATE HOMOPOLYMER OR COPOLYMER USING THE SAME**

(75) Inventors: Taek-Ho Yang, Daejeon (KR); Hye-Ok Kang, Daejeon (KR); Si-Jae Park, Daejeon (KR); Sang-Hyun Lee, Daejeon (KR); Eun-Jeong Lee, Daejeon (KR); Tae-wan Kim, Daejeon (KR); Sang-Yup Lee, Daejeon (KR)

(73) Assignee: LG Chem, Ltd., Seoul (KR)

( * ) Notice: Subject to any disclaimer, the term of this patent is extended or adjusted under 35 U.S.C. 154(b) by 919 days.

(21) Appl. No.: 12/312,676

(22) PCT Filed: Nov. 21, 2007

(86) PCT No.: PCT/KR2007/005858
§ 371 (c)(1),
(2), (4) Date: Sep. 28, 2009

(87) PCT Pub. No.: WO2008/062999
PCT Pub. Date: May 29, 2008

(65) Prior Publication Data
US 2010/0050298 A1   Feb. 25, 2010

(30) Foreign Application Priority Data

Nov. 23, 2006 (KR) .................. 10-2006-0116234

(51) Int. Cl.
*C12N 15/31* (2006.01)
*C12N 15/52* (2006.01)
*C12N 15/82* (2006.01)

(52) U.S. Cl.
USPC .......... 800/288; 800/284; 800/298; 536/23.2; 536/23.7; 435/252.3; 435/320.1; 435/419

(58) Field of Classification Search
USPC ............... 536/23.2, 23.7; 800/281, 284, 288, 800/298; 435/139, 183, 320.1, 419
See application file for complete search history.

(56) References Cited

FOREIGN PATENT DOCUMENTS

| JP | 2001-275671 | 10/2001 |
| WO | WO 2008/062995 A1 | 5/2008 |
| WO | WO 2009/031762 A2 | 3/2009 |

OTHER PUBLICATIONS

Steinbuchel and Hein, Advances in Biochemical Engineering/Biotechnology 2001, vol. 71; Sheper, Th., Ed., pp. 81-119.*
Taguchi, S. et al. Macromol. Biosci. 2004; vol. 4, pp. 145-156.*
Takeharu Tsuge, et al., "Mutation Effects of a Conserved Alanine (Ala510) in Type I Polyhydroxyalkanoate Synthase from *Ralstonia eutropha* on Polyester Biosynthesis", Macromolecular Bioscience Oct. 20, 2004, vol. 4, No. 10, Oct. 20, 2004, pp. 963-970, XP-002560665.
Henry E. Valentin, et al., "Application of enzymatically synthesized short-chain-length hydroxyl fatty acid coenzyme A thioesters for assay of polyhydroxyalkanoic acid synthases", Applied Microbiology and Biotechnology, Springer Verlag, Berlin, DE, vol. 40, No. 5, Jan. 1, 1994, pp. 699-709, XP-009127287.

* cited by examiner

*Primary Examiner* — Russell Kallis
(74) *Attorney, Agent, or Firm* — McKenna Long & Aldridge, LLP

(57) ABSTRACT

The present invention relates to polyhydroxyalkanoate synthase (PHA synthase) mutant originated from *Pseudomonas* sp. 6-19 (KCTC 11027BP) which can prepare lactate polymer and/or copolymer by using lactyl-CoA as a substrate. The present invention relates to a method for preparing lactate polymer and/or copolymer with the synthase mutant. The polyhydroxyalkanoate synthase mutants of the present invention originated from *Pseudomonas* sp. 6-19 can efficiently prepare lactate polymer and/or copolymer by using as a substrate lactyl-CoA which is difficult to be used as a substrate by conventional polyhydroxyalkanoate synthase.

8 Claims, 3 Drawing Sheets

MUTANTS OF PHA SYNTHASE FROM *PSEUDOMONAS* SP. 6-19 AND METHOD FOR PREPARING LACTATE HOMOPOLYMER OR COPOLYMER USING THE SAME This application claims the benefit of International PCT/KR2007/005858 filed on Nov. 21, 2007 along with KR 10-2006-0116234, filed Nov. 23, 2006, and are hereby incorporated by reference for all purposes as if fully set forth herein.

TECHNICAL FIELD

The present invention relates to polyhydroxyalkanoate synthase mutants derived from *Pseudomonas* sp. 6-19, wherein the mutants can use lactyl-CoA as a substrate to produce lactate polymer and/or lactate copolymer. The present invention also relates to a method for preparing lactate polymer and/or lactate copolymer, wherein the method uses the polyhydroxyalkanoate synthase mutants.

BACKGROUND ART

Polylactate (PLA) is a typical biodegradable polymer originated from lactate, which has a variety of applications as a common or a medical polymer. At present, PLA is being prepared by polymerizing lactate which is produced by fermenting microorganisms, but only low molecular weight PLA (1000-5000 dalton) is produced by direct polymerization of lactate. To synthesize high molecular weight (>100,000 dalton) of PLA, a method polymerizing low molecular weight PLA obtained by direct polymerization of lactate with a chain coupling agent can be used. However, it has disadvantages like that the process for preparing PLA of high molecular weight is complicated due to the addition of a solvent or a chain coupling agent, and also it isn't easy to remove them. At present, in the process for preparing commercially available PLA of high molecular weight, a method, in which lactate is converted into lactide to synthesize PLA by cyclodehydration of the lactide ring, is being used.

PLA homopolymer can be easily obtained from chemical synthesis method using lactate, but lactate compolymer having various monomer units is difficult to be produced and its commercial availability is very low.

Meanwhile, polyhydroxyalkanoate (PHA) is a polyester which microorganisms accumulate therein as a carbon and energy storage compound when other nutritive elements, for example, phosphorus, nitrogen, magnesium, oxygen, are deficient while the carbon source is in excess. PHA is recognized as an alternative material for synthesized plastics since it has similar properties to synthetic polymers originating from petroleum, and, at the same time, shows an excellent biodegradation property.

To produce PHA in microorganisms, an enzyme which converts microorganisms' metabolites into a PHA monomer and PHA synthase which synthesizes the PHA polymer using the PHA monomers are required. When producing PLA and lactate copolymer with microorganisms, the same system is needed and an enzyme being able to provide lactyl-CoA also is needed in addition to an enzyme providing hydroxyacyl-CoA, original substrate of PHA synthase.

On this account, the present inventors developed a system using propionyl-CoA transferase originated from *Clostridium propionicum* to provide lactyl-CoA and succeeded the production of PLA and lactate copolymer (Korean Patent Application laid-open No. 10-2006-0121555). However, it has little PHA synthase activity on hydroxyalkanoate which is hydroxylated at the 2-position. There have been reports of PHA synthase activity on lactyl-CoA measured in vitro, but PHA synthase activity on lactyl-CoA is reported to be very weak as said above (Zhang et al., *Appl. Microbiol. Biotechnol.*, 56:131, 2001; Valentin and Steinbuchel, *Appl. Microbiol. Biotechnol.*, 40:699, 1994; 및 Yuan et al. *Arch Biochem Biophys.* 394:87, 2001). Therefore, if a PHA synthase can not use lactyl-CoA efficiently and the PHA synthase is used to produce PLA and lactate copolymer, the synthesis efficiency must be low. That is, because lactate, hydroxyalkanoate which is hydroxylated at the 2-carbon position, is not a suitable substrate for PHA synthase, PHA synthase being able to use lactyl-CoA efficiently is very important to synthesize PLA and lactate copolymer efficiently.

DISCLOSURE

Technical Problem

Accordingly, the object of the present invention is to provide PHA synthase being able to efficiently use lactyl-CoA as a substrate.

Another object of the present invention is to provide a method for preparing PLA and lactate copolymer, wherein the method uses a cell or plant comprising genes of PHA synthase being able to use the lactyl-CoA as a substrate and propionyl-CoA transferase.

Technical Solution

To achieve the object, the present invention provides a polyhydroxyalkanoate synthase mutant using lactyl-CoA as a substrate to produce lactate polymer or lactate copolymer and having the amino acid sequence of SEQ. ID No: 10, wherein the glutamine at position 481 of the amino acid sequence of SEQ. ID No: 10 is mutated.

Preferably, the present invention provides the polyhydroxyalkanoate synthase mutant, wherein at least one amino acid selected from the group consisting of glutamate at position 130; serine at position 325; and serine at position 477 is further mutated.

More preferably, the present invention provides a polyhydroxyalkanoate synthase mutant using lactyl-CoA as a substrate to produce lactate polymer or lactate copolymer and having the amino acid sequence of SEQ. ID No: 10, wherein the amino acid sequence has any mutation of:
  a) S325T and Q481M;
  b) E130D and Q481K;
  c) S325T and Q481K;
  d) E130D and Q481M;
  e) E130D and Q481R;
  f) E130D, S325T and Q481M;
  g) E130D, S325T and Q481K;
  h) E130D, S477R and Q481K;
  i) E130D, S477R and Q481M;
  j) E130D, S477R and Q481R;
  k) E130D, S477H and Q481K;
  l) E130D, S477H and Q481M;
  m) E130D, S477H and Q481R;
  n) E130D, S477F and Q481K;
  o) E130D, S477F and Q481M;
  p) E130D, S477F and Q481R;
  q) E130D, S477Y and Q481K;
  r) E130D, S477Y and Q481M;
  s) E130D, S477Y and Q481R;
  t) E130D, S325T, S477R and Q481M;

u) E130D, S325T, S477R and Q481K;
v) E130D, S325T, S477F and Q481M;
w) E130D, S325T, S477G and Q481M; or
x) E130D, S325T, S477F and Q481K.

The present inventors confirmed that some mutants of polyhydroxyalkanoate synthase of *Pseudomonas* sp. 6-19 can use lactyl-CoA as a substrate and produce lactate polymer and/or copolymer very efficiently, thereby completing the present invention.

The present invention also provides a gene encoding the polyhydroxyalkanoate synthase mutant.

The present invention also provides a recombinant vector containing the gene for synthesizing lactate polymer or copolymer.

More preferably, the present invention provides the recombinant vector, further comprising a gene encoding propionyl-CoA transferase (pct).

The present invention also provides a cell or plant transformed with the above recombinant vector.

The present invention also provides a cell or plant obtained from transformation with the above recombinant vector, wherein the original cell or plant does not have a gene encoding propionyl-CoA transferase.

The present invention also provides a method for preparing lactate polymer or copolymer, wherein the method comprises culturing the cell or plant.

More preferably, the present invention provides the method, wherein the culturing is performed in a medium comprising 3-hydroxybutyrate (3-HB) and made copolymer is a copolymer comprising 3-hydroxybutyrate monomer unit and lactate monomer unit.

The term "copolymer," as used herein, is meant to include bipolymer consisting of two distinct monomers, terpolymer consisting of three distinct monomers or tetrapolymer consisting of four distinct monomers.

In the present invention, the hydroxyalkanoate is at least one selected from the group consisting of 3-hydroxybutyrate, 3-hydroxyvalerate, 4-hydroxybutyrate, (D)-3-hydroxycarboxylic acid of the medium chain length ($C_{6\sim14}$), 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 4-hydroxyvaleric acid, 4-hydroxyhexanoic acid, 4-hydroxyheptanoic acid, 4-hydroxyoctanoic acid, 4-hydroxydecanoic acid, 5-hydroxyvaleric acid, 5-hydroxyhexanoic acid, 6-hydroxydodecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methyl ester, 3-hydroxyadipinic acid-methyl ester, 3-hydroxysuberic acid-methyl ester, 3-hydroxyazelaic acid-methyl ester, 3-hydroxysebacic acid-methyl ester, 3-hydroxysuberic acid-ethyl ester, 3-hydroxysebacic acid-ethyl ester, 3-hydroxypimelic acid-propyl ester, 3-hydroxysebacic acid-benzyl ester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 6-hydroxy-3-dodecenoic acid, 3-hydroxy-2-methylbutyric acid, 3-hydroxy-2-methylvaleric acid and 3-hydroxy-2,6-dimethyl-5-heptenoic acid.

The present invention also provides a method for preparing lactate polymer or lactate copolymer, wherein the method comprises culturing the cell or plant.

The term "vector," as used herein, means a DNA construct comprising DNA sequence operably linked to a suitable control sequence capable of expressing the DNA in a suitable host. In the present invention, vector may be plasmid, bacteriophage, or simple genome insertion. If a suitable host is transformed with it, vector can replicate itself and operate irrespective of host genome, or in some cases, vector merges with host genome. Because plasmid is currently most often used as vector, plasmid herein is interchangeably used for vector. However, the vector according to the present invention includes a different type of vector having the same function, which is already known or will be known to the skilled person in the art.

The phrase "expression control sequence" means an DNA sequence essential for the expression of an operably linked coding sequence in a specific host. Such control sequence comprises a promoter for performing transcription; an arbitrary operator sequence for controlling the transcription; a sequence encoding binding site of a suitable mRNA ribosome; and a sequence for controlling the termination of transcription and translation. For example, control sequence suitable for prokaryote comprises a promoter, an arbitrary operator sequence and ribosome binding site. A promoter, a polyadenylated signal and an enhancer are comprised for eukaryote. In plasmid, the promoter is a factor that most severely affects the expression amount of gene. Preferably, SRα promoter, cytomegalovirus-derived promoter, etc. are used as a promoter for high expression.

Any one among various expression control sequences can be used in the vector to express the DNA sequence of the present invention. Examples of useful expression control sequence, for example, include the SV40 or the early and late promoters of adenovirus, the lac system, the trp system, the TAC or TRC system, the T3 and T7 promoters, the major operator and promoter region of phage lamda, the control region of fd code protein, the promoter for 3-phosphoglycerate kinase or other glycolytic enzymes, the promoters of the phosphatases, for example Pho5, the promoter of yeast alpha-mating system and the sequence of construct known for controlling the expression of genes of eukaryote, prokaryote or virus thereof, and their various combinations.

Nucleic acid is "operably linked" when it is placed into a functional relationship with another nucleic acid sequence. This may mean the way in which gene and control sequence (s) are linked, in that the expression of the gene is possible when a suitable molecule (for example, transcription-activating protein) is combined with control sequence(s). For example, DNA for a pre-sequence or secretory leader is operably linked to DNA for a polypeptide if it is expressed as a preprotein that participates in the secretion of the polypeptide; a promoter or enhancer is operably linked to a coding sequence if it affects the transcription of the sequence; or a ribosome binding site is operably linked to a coding sequence if it is positioned so as to facilitate translation. Generally, "operably linked" means that the DNA sequences being linked are contiguous, and, in the case of a secretory leader, contiguous and in reading phase. However, enhancers do not have to be contiguous. Linking is accomplished by ligation at convenient restriction sites. If such sites do not exist, the synthetic oligonucleotide adaptors or linkers are used in accordance with conventional practice.

The term "expression vector," as used herein, generally indicates double-stranded DNA fragment as a recombinant carrier in which typically heterologous DNA fragment is inserted. The heterologous DNA means a hetero-type DNA which is not naturally occurring in host cells. Once the expression vector is incorporated into the host cell, it can be replicated regardless of host chromosomal DNA to produce several copies and heterologous DNA inserted into them.

As known to those skilled in the related art, to increase the expression level of gene transfected in host cell, corresponding gene should be operably connected to sequence for control transcription and decoding expression, which functions in selected expression host. Preferably, expression control sequence and corresponding gene are contained in one expression vector comprising virus selection marker and replication origin together. If expression host is eukaryotes, expression vector should further comprise expression marker useful in eukaryote expression host.

In the present invention, various vectors like plasmid vector, bacteriophage vector, cosmid vector, or YAC (Yeast Artificial Chromosome) vector can be used as the above vector. It is preferable to use plasmid vector for the purpose of the present invention. Typical plasmid vectors that can be used for these purposes have (a) an origin of replication so that it leads to effective replication so that each host cell contains several hundred copies of plasmid vector, (b) an antibiotic-resistance gene so that a host cell transformed with a plasmid vector can be selected and (c) a sequence comprising a restriction enzyme site where a foreign DNA fragment is to be inserted. Even in the absence of a suitable restriction enzyme site, a vector or foreign DNA can easily be ligated by using a synthetic oligonucleotide adaptor or a linker according to conventional methods.

A recombinant vector of the present invention can be transformed into a suitable host cell according to methods known in the art. Preferable host cell in the present invention is prokaryotic cell, more preferably, E. coli. Preferable strains of E. coli include: E. coli DH5a, E. coli JM101, E. coli K12, E. coli W3110, E. coli X1776, E. coli XL1-Blue (Stratagene) and E. coli B. However, other E. coli strains such as FMB101, NM522, NM538 and NM539 and other prokaryotic species and genera can also be used. In addition to E. coli said above, the genus *Agrobacterium*, such as *Agrobacterium* A4, the genus *Bacilli*, such as *Bacillus subtilis*, various enterobacteria such as *Salmonella typhimurium* or *Serratia marcescens* and the various genuses *Pseudomonas* can be used herein as host cells, but the scope of the present invention is not limited to examples said above.

In addition, the transformation of prokaryotes can be easily performed according to calcium chloride method described in section 1.82 of Sambrook et al. (supra). Alternatively, electroporation (Neumann et al., EMBO J., 1: 841(1982)) also can be used to transform these kinds of cells.

Transformation of plants for preparing plant comprising genes of transferase and synthase can be achieved by conventional methods using *Agrobacterium* or virus vectors. For example, transformed plants are obtained by transforming an *Agrobacterium* with a recombinant vector containing the inventive gene and infecting a tissue, etc. of the target plant with the transformed *Agrobacterium*. More specifically, the transformed plant can be prepared by (a) pre-culturing an explant of plant of interest, and then transforming the explant by co-cultivating the explant and a transformed *Agrobacterium*; (b) culturing said infected explants to induce callus; and (c) excising obtained callus, and culturing it in shoot-inducing medium.

The term "explant," as used herein, means a tissue fragment cut from a plant, and includes cotyledon or hypocotyl. Cotyledon or hypocotyls can be used as the explant of the present invention. It is more preferable to use cotyledon obtained by disinfecting and washing seeds of the plant, and germinating it in MS medium.

Transformed plants useful for the present invention include, but are not limited to, tobacco, tomato, red peppers, beans, nice, and corn. Also, even though a transformed plant is one that propagates sexually, it will be obvious to a person skilled in the art that such a plant can be reproduced asexually using plant tissue culture, etc.

MODES FOR CARRYING OUT THE INVENTION

Hereinafter, the present invention is described in considerable detail. The following examples are offered by way of illustration to help those skilled in the art understand the present invention, and are not intended to limit the scope of the invention.

Particularly, although the synthesis of poly(3-hydroxybutyrate-co-lactate) (P(3HB-co-LA)) obtained by adding 3-hydroxybutyrate (3-HB) when preparing lactate copolymer with PHA synthase mutant is disclosed in the following examples, it will be obvious to those skilled in the art of the present invention that various copolymer comprising different hydroxyalkanoate and lactate can be prepared by adding other hydroxyalkanoate except 3-HB.

Example 1

Cloning of PHA Synthase Gene Originated from Pseudomonas sp. 6-19 and Construction of Expression Vector To separate the gene of PHA synthase (phaC1$_{Ps6-19}$) originated from Pseudomonas sp. 6-19 (KCTC 11027BP), total DNA of Pseudomonas sp. 6-19 was extracted, and the primers of SEQ ID NO: 1 and 2 were prepared based on the sequence of phaC1$_{Ps6-19}$ gene (Ae-jin Song, Master's Thesis, Department of Chemical and Biomolecular Engineering, KAIST, 2004) and PCR was performed to get the gene of phaC1$_{Ps6-19}$.

```
SEQ ID NO: 1: 5-GAG AGA CAA TCA AAT CAT GAG TAA CAA
              GAG TAA CG-3

SEQ ID NO: 2: 5-CAC TCA TGC AAG CGT CAC CGT TCG TGC
              ACG TAC-3
```

Figure 1:
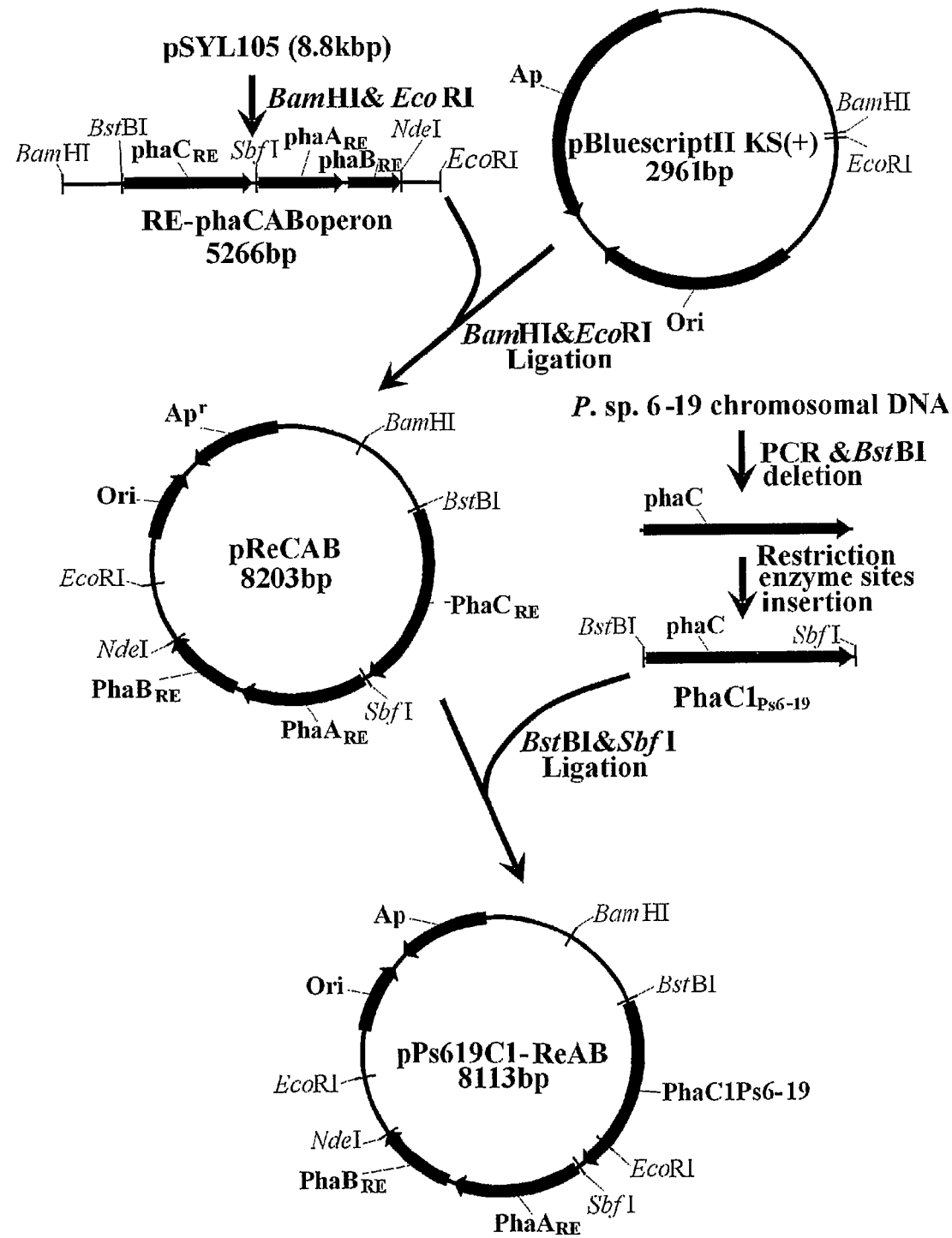
FIG. 1 is a diagram showing preparing process of a recombinant expression vector comprising the gene of polyhydroxyalkanoate synthase originated from *Peudomonas* sp. 6-19.

As a result of examining PCR reaction product by agarose gel electrophoresis, 1.7 Kbp gene fragment corresponding to phaC1$_{Ps6-19}$ gene was observed. The operon of constitutive expression system expressing enzyme supplying monomer and synthase was constructed for expression of phaC1$_{Ps6-19}$ synthase (FIG. 1).

DNA fragment comprising PHB-synthesizing operon originated from Ralstonia eutropha H16 was excised with BamHI/EcoRI from pSYL105 vector (Lee et al., Biotech. Bioeng., 1994, 44:1337-1347), and was inserted into the BamHI/EcoRI-recognition site of pBluescript II (Stratagene) to construct the pReCAB recombinant vector.

pReCAB vector is known to constitutively express PHA synthase (phaC$_{RE}$) and monomer-supplying enzyme (phaA$_{RE}$ and phaB$_{RE}$) by PHB operon promoter and also known to well operate in E. Coli (Lee et al., Biotech. Bioeng., 1994, 44:1337-1347). pReCAB vector was excised with BstBI/SbfI to delete R. eutropha H16 PHA synthase (phaC$_{RE}$), and then the above phaC1$_{Ps6-19}$ gene was inserted into BstBI/SbfI site to make pPs619C1-ReAB recombinant vector (FIG. 1).

BstBI sites contained inside were removed by SDM (site directed mutagenesis) method without mutation of amino acid to make phaC1$_{Ps6-19}$ synthase gene fragment having two BstBI/SbfI sites at the both ends, and overlapping PCR were performed with the primers of SEQ ID NO: 3 and 4, SEQ ID NO: 5 and 6, and SEQ ID NO: 7 and 8 to add BstBI/SbfI-recognition site

```
SEQ ID NO: 3: 5-atg ccc gga gcc ggt tcg aa-3

SEQ ID NO: 4: 5-CGT TAC TCT TGT TAC TCA TGA TTT GAT
              TGT CTC TC-3

SEQ ID NO: 5: 5-GAG AGA CAA TCA AAT CAT GAG TAA CAA
              GAG TAA CG-3

SEQ ID NO: 6: 5-CAC TCA TGC AAG CGT CAC CGT TCG TGC
              ACG TAC-3

SEQ ID NO: 7: 5-GTA CGT GCA CGA ACG GTG ACG CTT GCA
              TGA GTG-3

SEQ ID NO: 8: 5-aac ggg agg gaa cct gca gg-3
```

The phaC1$_{Ps6-19}$ gene sequence of the pPs619C1-ReAB recombinant vector was confirmed by sequencing and the result was shown in SEQ ID NO: 9, by which the amino acid sequence encoded was shown in SEQ ID NO: 10.

The similarity test of the sequences showed that the gene has 84.3% nucleotide sequence identity and 88.9% amino acid sequence identity with phaC1 originated from Pseudomonas sp. strain 61-3 (Matsusaki et al., J. Bacteriol., 180:6459, 1998), from which it was confirmed that the two synthases were very similar. From these results, the phaC1$_{Ps6-19}$ synthase obtained in the present invention was confirmed to be Type II PHA synthase.

To confirm whether the phaC1$_{Ps6-19}$ synthase synthesize PHB or not, E. coli XL-1Blue (Stratagene) was transformed with the pPs619C1-ReAB recombinant vector, and cultured in PHB detection medium (LB agar, glucose 20 g/L, Nile red 0.5 ug/ml). As a result of that, the synthesis of PHB was not observed.

Example 2

Preparation of Substrate-specific Mutant of PHA Synthase Originated from Pseudomonas sp. 6-19

Type II PHA synthase among various kinds of PHA synthases is known to be MCL-PHA (medium-chain-length PHA) synthase being able to polymerize substrate having relatively long carbon chain. This MCL synthase is expected to be useful in preparing lactate polymer. Even if phaC1 synthase originated from Pseudomonas sp. 61-3, which having high identity with the phaC1$_{Ps6-19}$ synthase of the present invention, is Type II synthase, phaC1 synthase is reported to have relatively broad range of substrate-specificity (Matsusaki et al., J. Bacteriol., 180:6459, 1998), and a study on its mutant suitable for preparing SCL-PHA (short-chain-length PHA) was reported (Takase et al., Biomacromolecules, 5:480, 2004). Based on these results, three positions of amino acid affecting SCL activity were found out through sequence alignment analysis, and phaC1$_{Ps6-19}$ synthase mutants shown in table 1 below were prepared by SDM method using the primers of SEQ ID NO: 11 to 14.

TABLE 1

| Recombinant vector | Necleic acid substitution | Amino acid substitution | Primer |
|---|---|---|---|
| pPs619C1200-ReAB | AGC →ACC | S325T | SEQ ID NO: 11/12 |
|  | CAG →ATG | Q481M | SEQ ID NO: 13/14 |
| pPs619C1300-ReAB | GAA →GAT | E130D | SEQ ID NO: 15/16 |
|  | AGC →ACC | S325T | SEQ ID NO: 11/12 |
|  | CAG →ATG | Q481M | SEQ ID NO: 13/14 |

```
SEQ ID NO: 11: 5-CTG ACC TTG CTG GTG ACC GTG CTT GAT ACC ACC-3
SEQ ID NO: 12: 5-GGT GGT ATC AAG CAC GGT CAC CAG CAA GGT CAG-3
SEQ ID NO: 13: 5-CGA GCA GCG GGC ATA TC A TGA GCA TCC TGA ACC CGC-3
SEQ ID NO: 14: 5-GCG GGT TCA GGA TGC TCA TGA TAT GCC CGC TGC TCG-3
SEQ ID NO: 15: 5-atc aac ctc atg acc gat gcg atg gcg ccg acc-3
SEQ ID NO: 16: 5-ggt cgg cgc cat cgc atc ggt cat gag gtt gat-3
```

Figure 2:
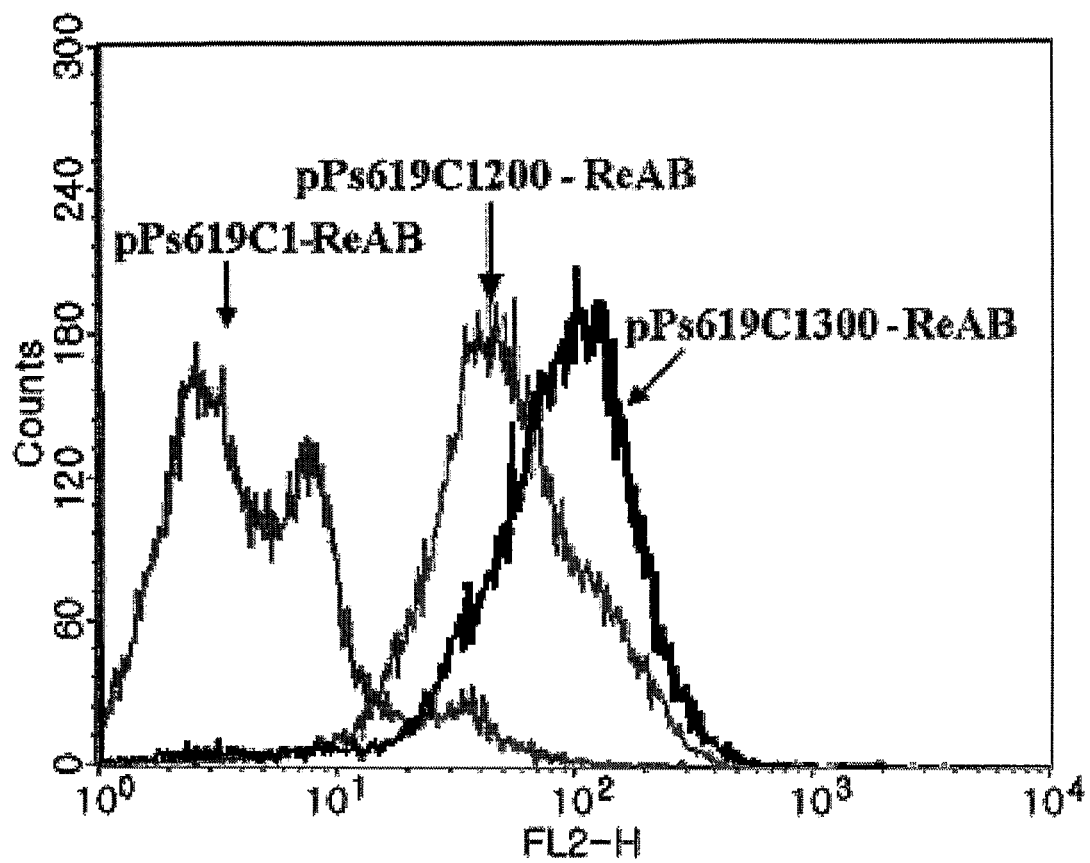
FIG. 2 is FACS (Florescence Activated Cell Sorting) results after the culturing of E. Coli transformed with recombinant vectors (pPs619C1-ReAB, pPs619C1200-ReAB and pPs619C1300-ReAB) comprising phaC1$_{Ps6-19}$ synthase and SCL mutants (phaC1$_{Ps6-19}$200 and phaC1$_{Ps6-19}$300), in the condition of being able to synthesize PHB.

E. coli XL-1Blue was transformed with these recombinant vectors, and cultured in PHB detection medium (LB agar, glucose 20 g/L, Nile red 0.5 ug/ml). PHB synthesis was observed in both E. coli XL-1Blue transformed with pPs619C1200-ReAB and E. coli XL-1Blue transformed with pPs619C1300-ReAB. That is, 3HB-CoA was made from glucose by monomer-supplying enzymes of phaA$_{RE}$ and phaB$_{RE}$, and the 3HB-CoA was used as substrate by phaC1$_{Ps6-19}$ synthase SCL mutants (phaC1$_{Ps6-19}$200 and phaC1$_{Ps6-19}$300) to make PHB. For quantitative analysis, transformed recombinant E. Coli XL1-Blue was cultured for 4 days in LB medium comprising glucose (20 g/L) at 37° C. Cultured recombinant E. Coli was given sucrose shock and stained with Nile-red, which was analyzed by FACS (Florescence Activated Cell Sorting) (FIG. 2).

E. Coli XL1-Blue transformed with pPs619C1-ReAB vector comprising wild synthase was not stained with Nile-red, while E. Coli XL1-Blue transformed with pPs619C1200-ReAB or pPs619C1300-ReAB showed high fluorescence because of PHB stained with Nile-red in cell. Further, the content of PHB made in cell was evaluated by collecting cultured microorganism through centrifugation, drying them for 48 hours in dryer of 80° C., and then performing gas chromatography analysis. The content of PHB was 29.7% (w/w) and 43.1% (w/w) in E. Coli XL1-Blue transformed with pPs619C1200-ReAB and pPs619C1300-ReAB, respectively, and PHB was not detected in the case of pPs619C1-ReAB.

Example 3

Figure 3:
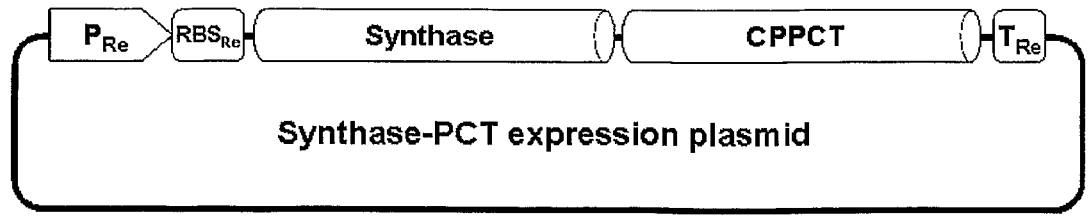
FIG. 3 is a simple diagram of constitutive expression vector expressing PHA synthase and CP-PCT together.
Figure 4:
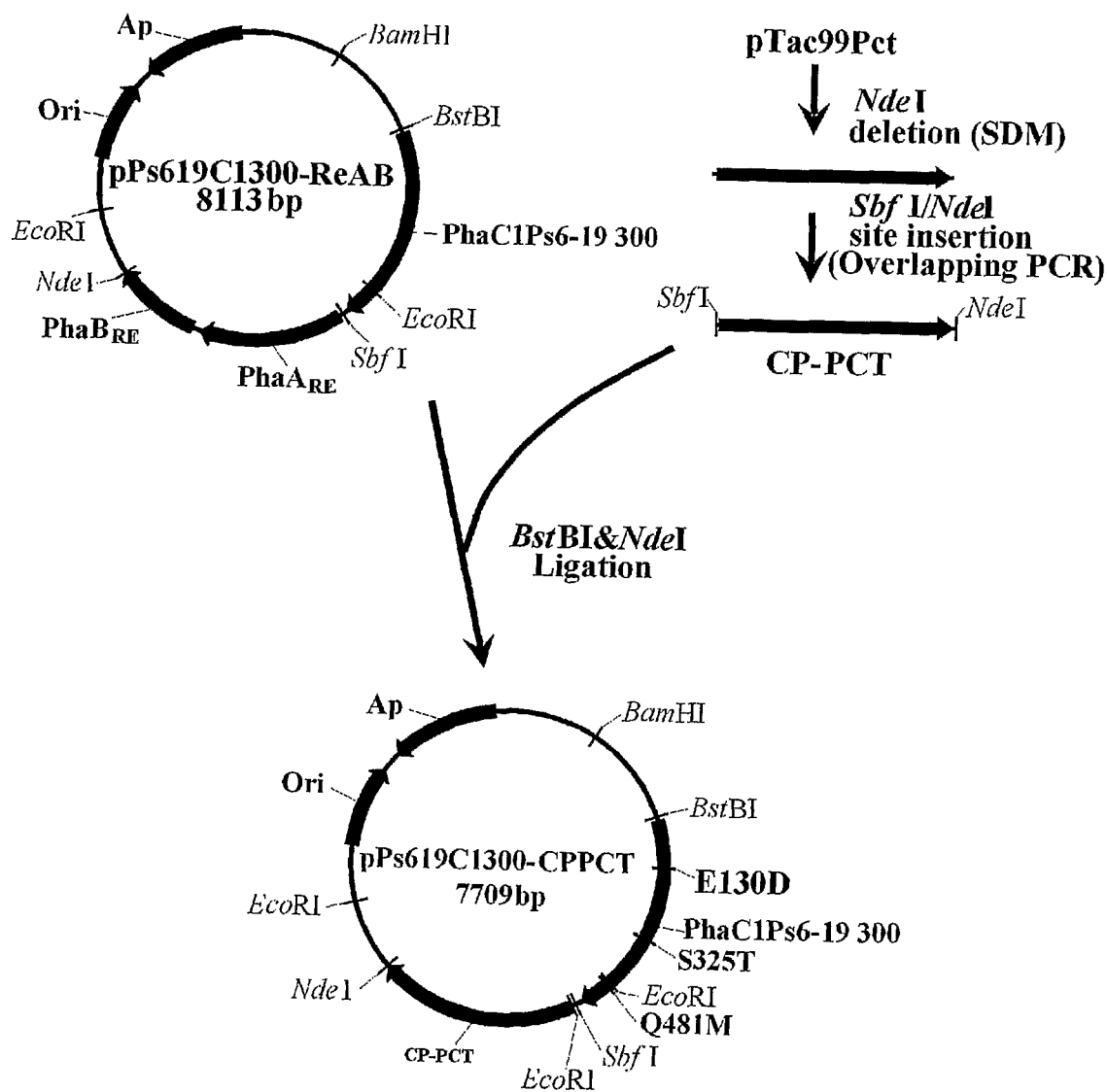
FIG. 4 is a diagram showing preparing process of a recombinant expression vector comprising the genes of PHA synthase originated from *Peudomonas* sp. 6-19, SCL mutant and CP-PCT.

Construction of Recombinant E. Coli being able to Express PHA Synthase Originated from Pseudomonas sp. 6-19 and Propionyl-CoA Transferase, and Preparation of PLA or Lactate Copolymer using the same In this example, propionyl-CoA transferase originated from Clostridium propionicum (CP-PCT) was used to supply lactyl-CoA, a monomer needed for synthesis of PLA and lactate copolymer. The operon of constitutive expression system expressing PHA synthase and CP-PCT together was constructed like FIG. 3. CP-PCT was well known to have toxicity to microorganism. That is, in tac promoter or T7 promoter expression system induced by IPTG (this system is widely used in expression of recombinant protein), all microorganisms become dead shortly after the addition of inducer. Because of this reason, it is thought as suitable to use expression system in which it is weakly expressed, but continuously expressed according to the growth of microorganism. The fragment obtained through PCR performed with chromosome DNA of Clostridium propionicum and the primers of SEQ ID NO: 17 and 18 was used as cp-pct, and NdeI site of wild CP-PCT was removed by SDM method for easiness of cloning (FIG. 4).

SEQ ID NO: 17: 5-ggaattcATGAGAAAGGTTCCCATTATTACCGC
              AGATGA

SEQ ID NO: 18: 5-gc tctaga tta gga ctt cat ttc ctt
              cag acc cat taa gcc ttc tg In addition, overlapping PCR was performed with the primers of SEQ ID NO: 19 and 20 to add SbfI/NdeI recognition site.

SEQ ID NO: 19:  5-agg cct gca ggc gga taa caa ttt
               cac aca gg-3

SEQ ID NO: 20:  5-gcc cat atg tct aga tta gga ctt
               cat ttc c-3 pPs619C1300-ReAB vector comprising phaC1$_{Ps6-19}$ synthase SCL mutant, phaC1$_{Ps6-19}$300, was excised with SbfI/NdeI to remove monomer-supplying enzymes (phaA$_{RE}$ and phaB$_{RE}$) originated from Ralstonia eutrophus H16, and then the PCT-cloned CP-PCT gene was inserted into SbfI/NdeI site to make pPs619C1300-CPPCT recombinant vector (FIG. 4).

In addition, pPs619C1200-CPPCT recombinant vector comprising another phaC1$_{Ps6-19}$ synthase SCL mutant, phaC1$_{Ps6-19}$200, and pPs619C1-CPPCT recombinant vector comprising wild phaC1$_{Ps6-19}$ synthase were made by the above same method. To confirm whether the polymer is made or not through the supply of monomer by CP-PCT, E. coli XL-1Blue was transformed with pPs619C1200-CPPCT and pPs619C1300-CPPCT recombinant vector, was cultured in PHB detection medium (LB agar, glucose 20 g/L, 3HB 2 g/L, Nile red 0.5 µg/ml). As a result of that, the synthesis of PHB was observed in both.

With the pPs619C1300-CPPCT recombinant vector, flask cultures were performed in various conditions to make PLA and lactate copolymer. Results were shown in table 2 below.

TABLE 2

| Strain | Medium | Culture | Substrate | PHB Content (%) | PLA Content (%) |
|---|---|---|---|---|---|
| XL1-Blue | LB glucose (10 g/L) | aerobic | lactate (5 g/L) | — | 0.6 |
| XL1-Blue | LB→MR glucose (20 g/L) | 2 steps (aerobic →anaerobic) | — | — | 1 |
| Top 10 | LB→MR glucose (20 g/L) | 2 steps (aerobic →anaerobic) | — | — | 0.3 |
| XL1-Blue | LB→MR glucose (20 g/L) | 2 steps (aerobic →anaerobic) | 3HB (2 g/L) | 3.19 | 2.75 |
| Top 10 | LB→MR glucose (20 g/L) | 2 steps (aerobic →anaerobic) | 3HB (2 g/L) | 2.84 | 3.1 |
| Top 10 | LB glucose (20 g/L) | aerobic | 3HB (0.05 g/L) Lactate (5 g/L) | 0.07 | 1.97 |
| Top 10 | LB glucose (20 g/L) | aerobic | 3HB (0.2 g/L) lactate (5 g/L) | 0.31 | 3.18 |

The 2 steps culture was performed by replacing culture medium with MR medium and then trying anaerobic culture to make lactate in cell. As a result of culturing recombinant E. Coli in various conditions, PLA homopolymer was prepared about 1%, and lactate copolymer made by adding 3HB as substrate was prepared about 6% based on the weight of dried cells. The composition of MR medium used in the fed-batch culture according to the present invention was shown in table 3 below.

TABLE 3

| Ingredient | Modified R (MR) (/L) |
|---|---|
| KH$_2$PO$_4$ | 6.67 g |
| (NH$_4$)$_2$HPO$_4$ | 4 g |
| Citrate | 0.8 g |
| MgSO$_4$•H$_2$O | 0.8 g |
| 3HB | 0 or 0.2 g |
| Glucose | 50 g |
| Microingredient* | 5 mL |

*Microingredient (/L): FeSO$_4$•H$_2$O, 10 g; ZnSO$_4$•H$_2$O, 2.25 g; CuSO$_4$•H$_2$O, 1 g; MnSO$_4$•H$_2$O, 0.5 g; CaCl$_2$•H$_2$O, 2 g; Na$_2$B$_4$O$_7$•H$_2$O, 0.23 g; (NH$_4$)$_6$Mo$_7$O$_{24}$, 0.1 g; 35% HCl, 10 mL.

Example 4

Preparation of P(3HB-co-LA) Copolymer Through Fed-batch Culture of Recombinant E. Coli Recombinant *E. Coli* (transformed with pPs619C1300-CPPCT vector) was cultured at 37° C., for 12 hours, at the stirring speed of 200 rpm in 3 mL of LB medium comprising 20 g/L of glucose, 100 mg/L of ampicillin, etc. This medium was inoculated in 100 mL of the same medium, and cultured for 6 hours in the same condition. The final medium was used as seed culture of fed-batch culture. MR medium was used as starting medium for fed-batch culture. Fed-batch culture was started by inoculating 100 mL of the seed culture into 2.4 L of MR medium. The temperature of medium was 37° C., and the pH was adjusted to 6.8-6.9 with 14% ammonia aqueous solution, and dissolved oxygen was maintained over 20% of saturated air by controlling the supply of air and stirring speed. At this time, the speed of supplying air was 1 vvm. When glucose contained in the starting medium was exhausted, 20 g of glucose and 5 g of 3-hydroxybutyrate (3HB) were supplied, and at the same time the stirring speed was made to 200 rpm and the speed of supplying air was decreased to 0.1 vvm to change aerobic condition to anaerobic condition. For total culture, glucose was supplied 5 times. 5 g of 3HB was supplied together at the first and third times among 5 times. After the termination of culture, cells were collected by centrifugation, and freeze-dried.

To refine the prepared polymer, the polymer was extracted from the freeze-dried cells by a Soxhlet extractor using chloroform. Then, a large part of chloroform was removed from the chloroform solution dissolving the polymer by a rotary evaporator, and methanol wad added to the remaining solution to precipitate the polymer. The precipitated polymer was filtered, and dried for 12 hours in a vacuum-drier.

In addition, some part of the cells obtained by centrifugation was dried at a dryer of 80° C. for 48 hours, and the content of P(3HB-co-LA) copolymer in cells was analyzed by gas chromatography. PLA homopolymer and P(3HB-co-3HV) copolymer, in which the content of 3HV is 12 wt %, were used as standard.

As a result, the content of the synthesized P(3HB-co-LA) in *E. Coli* was about 10% based on the weight of dried cells, and the content of PLA in the copolymer was 88 mol %.

From this example performing gas chromatography of the finally obtained polymer, the obtained polymer was confirmed to be P(3HB-co-LA) copolymer and the content of PLA in the copolymer was confirmed to be 88 mol %.

Example 5

Preparation of PLA Homopolymer by Fed-batch Culture of the Recombinant E. Coli According to the method of example 4, the seed culture of the recombinant *E. Coli* transformed with pPs619C1300-CPPCT vector was performed, and fed-batch culture was started by inoculating 100 mL of the seed culture medium into 2.4 L of MR medium. The temperature of medium was 37° C., and the pH was adjusted to 6.8-6.9 with 14% ammonia aqueous solution, and dissolved oxygen was maintained over 20% of saturated air by controlling the supply of air and stirring speed. At this time, the speed of supplying air was 1 vvm. When glucose contained in the starting medium was exhausted, 20 g of glucose was supplied, and at the same time the stirring speed was made to 200 rpm and the speed of supplying air was decreased to 0.1 vvm to change aerobic condition to anaerobic condition. For total culture, glucose was supplied 5 times. After the termination of culture, cells were collected by centrifugation, and freeze-dried. The polymer was collected according to the method of example 4.

In addition, some part of the cells obtained by centrifugation was dried at a dryer of 80° C. for 48 hours, and the content of PLA in cells was analyzed by gas chromatography. Methyl-4HB, PLA homopolymer and P(3HB-co-3HV) copolymer, in which the content of 3HV is 12 wt %, were used as standard.

As a result, 3HB and 4HB were not detected, and only PLA was observed. The content of the synthesized PLA in *E. Coli* was about 10% based on the weight of dried cells. From gas chromatography results of the finally obtained polymer, the obtained polymer was observed to be polylactate polymer in which the content of PLA was 99.1 mol %.

Example 6

Preparation of Various Mutants

Various PHA synthase mutants were prepared according to the same method disclosed in the above example 2 with the primers below. Obtained mutants were shown in tables 4, 5, 6 and 7.

```
E130D
SEQ ID NO: 15: 5'-atc aac ctc atg acc gat gcg atg gcg ccg acc-
                   3'

SEQ ID NO: 16: 5'-ggt cgg cgc cat cgc atc ggt cat gag gtt gat-
                   3'

S325T
SEQ ID NO: 11: 5'-CTG ACC TTG CTG GTG ACC GTG CTT GAT ACC ACC-
                   3'

SEQ ID NO: 12: 5'-GGT GGT ATC AAG CAC GGT CAC CAG CAA GGT CAG-
                   3'

S477R
SEQ ID NO: 21: 5'-gaa ttc gtg ctg tcg agc cgc ggg cat atc-3'

SEQ ID NO: 22: 5'-gat atg ccc gcg gct cga cag cac gaa ttc-3'

S477H
SEQ ID NO: 23: 5'-gaa ttc gtg ctg tcg agc cat ggg cat atc-3'

SEQ ID NO: 24: 5'-gat atg ccc atg gct cga cag cac gaa ttc-3'
```

-continued

S477F
SEQ ID NO: 25: 5'-gaa ttc gtg ctg tcg agc ttt ggg cat atc-3'

SEQ ID NO: 26: 5'-gat atg ccc aaa gct cga cag cac gaa ttc-3'

S477Y
SEQ ID NO: 27: 5'-gaa ttc gtg ctg tcg agc tat ggg cat atc-3'

SEQ ID NO: 28: 5'-gat atg ccc ata gct cga cag cac gaa ttc-3'

S477G
SEQ ID NO: 29: 5'-gaa ttc gtg ctg tcg agc ggc ggg cat atc-3'

SEQ ID NO: 30: 5'-gat atg ccc gcc gct cga cag cac gaa ttc-3'

Q481K
SEQ ID NO: 31: 5'-ggg cat atc aaa agc atc ctg aac ccg c-3'

SEQ ID NO: 32: 5'-gcg ggt tca gga tgc ttt tga tat gcc c-3'

Q481M
SEQ ID NO: 33: 5'-ggg cat atc atg agc atc ctg aac ccg c-3'

SEQ ID NO: 34: 5'-gcg ggt tca gga tgc tca tga tat gcc c-3'

Q481R
SEQ ID NO: 35: 5'-ggg cat atc cgc agc atc ctg aac ccg c-3'

SEQ ID NO: 36: 5'-gcg ggt tca gga tgc tgc gga tat gcc c-3'

TABLE 4

| Recombinant synthase | Nucleic acid substitution | Amino acid substitution | Primers |
|---|---|---|---|
| pPs619C1200 | AGC → ACC | S325T | SEQ ID NO: 11, 12 |
| | CAG → ATG | Q481M | SEQ ID NO: 33, 34 |
| pPs619C1202 | GAA → GAT | E130D | SEQ ID NO: 15, 16 |
| | CAG → AAA | Q481K | SEQ ID NO: 31, 32 |
| pPs619C1203 | AGC → ACC | S325T | SEQ ID NO: 11, 12 |
| | CAG → AAA | Q481K | SEQ ID NO: 31, 32 |
| pPs619c1204 | GAA → GAT | E130D | SEQ ID NO: 15, 16 |
| | CAG → ATG | Q481M | SEQ ID NO: 33, 34 |
| pPs619C1205 | GAA → GAT | E130D | SEQ ID NO: 15, 16 |
| | CAG → CGC | Q481R | SEQ ID NO: 35, 36 |

TABLE 5

| Recombinant synthase | Nucleic acid substitution | Amino acid substitution | Primers |
|---|---|---|---|
| pPs619C1300 | GAA → GAT | E130D | SEQ ID NO: 15, 16 |
| | AGC → ACC | S325T | SEQ ID NO: 11, 12 |
| | CAG → ATG | Q481M | SEQ ID NO: 33, 34 |
| pPs619C1301 | GAA → GAT | E130D | SEQ ID NO: 15, 16 |
| | AGC → ACC | S325T | SEQ ID NO: 11, 12 |
| | CAG → AAA | Q481K | SEQ ID NO: 31, 32 |
| pPs619C1304 | GAA → GAT | E130D | SEQ ID NO: 15, 16 |
| | AGC → CGC | S477R | SEQ ID NO: 21, 22 |
| | CAG → AAA | Q481K | SEQ ID NO: 31, 32 |
| pPs619C1305 | GAA → GAT | E130D | SEQ ID NO: 15, 16 |
| | AGC → CGC | S477R | SEQ ID NO: 21, 22 |
| | CAG → ATG | Q481M | SEQ ID NO: 33, 34 |
| pPs619C1306 | GAA → GAT | E130D | SEQ ID NO: 15, 16 |
| | AGC → CGC | S477R | SEQ ID NO: 21, 22 |
| | CAG → CGC | Q481R | SEQ ID NO: 35, 36 |
| pPs619C1307 | GAA → GAT | E130D | SEQ ID NO: 15, 16 |
| | AGC → CAT | S477H | SEQ ID NO: 23, 24 |
| | CAG → AAA | Q481K | SEQ ID NO: 31, 32 |
| pPs619C1308 | GAA → GAT | E130D | SEQ ID NO: 15, 16 |
| | AGC → CAT | S477H | SEQ ID NO: 23, 24 |
| | CAG → ATG | Q481M | SEQ ID NO: 33, 34 |
| pPs619C1309 | GAA → GAT | E130D | SEQ ID NO: 15, 16 |
| | AGC → CAT | S477H | SEQ ID NO: 23, 24 |
| | CAG → CGC | Q481R | SEQ ID NO: 35, 36 |
| pPs619C1310 | GAA → GAT | E130D | SEQ ID NO: 15, 16 |
| | AGC → TTT | S477F | SEQ ID NO: 25, 26 |
| | CAG → AAA | Q481K | SEQ ID NO: 31, 32 |

TABLE 6

| Recombinant synthase | Nucleic acid substitution | Amino acid substitution | Primers |
|---|---|---|---|
| pPs619C1311 | GAA → GAT | E130D | SEQ ID NO: 15, 16 |
| | AGC → TTT | S477F | SEQ ID NO: 25, 26 |
| | CAG → ATG | Q481M | SEQ ID NO: 33, 34 |
| pPs619C1312 | GAA → GAT | E130D | SEQ ID NO: 15, 16 |
| | AGC → TTT | S477F | SEQ ID NO: 25, 26 |
| | CAG → CGC | Q481R | SEQ ID NO: 35, 36 |
| pPs619C1313 | GAA → GAT | E130D | SEQ ID NO: 15, 16 |
| | AGC → TAT | S477Y | SEQ ID NO: 27, 28 |
| | CAG → AAA | Q481K | SEQ ID NO: 31, 32 |

TABLE 6-continued

| Recombinant synthase | Nucleic acid substitution | Amino acid substitution | Primers |
|---|---|---|---|
| pPs619C1314 | GAA → GAT | E130D | SEQ ID NO: 15, 16 |
| | AGC → TAT | S477Y | SEQ ID NO: 27, 28 |
| | CAG → ATG | Q481M | SEQ ID NO: 33, 34 |
| pPs619C1315 | GAA → GAT | E130D | SEQ ID NO: 15, 16 |
| | AGC → TAT | S477Y | SEQ ID NO: 27, 28 |
| | CAG → CGC | Q481R | SEQ ID NO: 35, 36 |

TABLE 7

| Recombinant synthase | Nucleic acid substitution | Amino acid substitution | Primers |
|---|---|---|---|
| pPs619C1400 | GAA → GAT | E130D | SEQ ID NO: 15, 16 |
| | AGC → ACC | S325T | SEQ ID NO: 11, 12 |
| | AGC → CGC | S477R | SEQ ID NO: 21, 22 |
| | CAG → ATG | Q481M | SEQ ID NO: 33, 34 |
| pPs619C1401 | GAA → GAT | E130D | SEQ ID NO: 15, 16 |
| | AGC → ACC | S325T | SEQ ID NO: 11, 12 |
| | AGC → CGC | S477R | SEQ ID NO: 21, 22 |
| | CAG → AAA | Q481K | SEQ ID NO: 31, 32 |
| pPs619C1334 | GAA → GAT | E130D | SEQ ID NO: 15, 16 |
| | AGC → ACC | S325T | SEQ ID NO: 11, 12 |
| | AGC → TTT | S477F | SEQ ID NO: 25, 26 |
| | CAG → ATG | Q481M | SEQ ID NO: 33, 34 |
| pPs619C1336 | GAA → GAT | E130D | SEQ ID NO: 15, 16 |
| | AGC → ACC | S325T | SEQ ID NO: 11, 12 |
| | AGC → GGC | S477G | SEQ ID NO: 29, 30 |
| | CAG → ATG | Q481M | SEQ ID NO: 33, 34 |
| pPs619C1339 | GAA → GAT | E130D | SEQ ID NO: 15, 16 |
| | AGC → ACC | S325T | SEQ ID NO: 11, 12 |
| | AGC → TTT | S477F | SEQ ID NO: 25, 26 |
| | CAG → AAA | Q481K | SEQ ID NO: 31, 32 |

Example 7

Synthesis of P(3HB-co-LA) using Various Mutants

According to the same method as described in the above example 3, recombinant *E. coli* being able to express PHA synthase mutant originated from *Pseudomonas* sp. 6-19 and propionyl-CoA transferase were constructed, and P(3HB-co-LA) were prepared with the recombinant *E. Coli* through the same method as described in the above example 4. Results were shown in table 8, 9 and 10.

TABLE 8

| Mutation | WT | E130 | S325 | S477 | Q481 | Content (wt %) | LA mol % |
|---|---|---|---|---|---|---|---|
| Double | C1-202 | D | | | K | 36.6 | 35.3 |
| | C1-204 | D | | | M | 28.2 | 19.7 |
| | C1-204 | D | | | M | 42.9 | 10.7 |
| | C1-205 | D | | | R | 22.9 | 35.1 |

TABLE 9

| Mutation | WT | E130 | S325 | S477 | Q481 | Content (wt %) | LA mol % |
|---|---|---|---|---|---|---|---|
| Triple | C1-300 | D | T | | M | 43.8 | 31.9 |
| | C1-304 | D | | R | K | 20.2 | 22.0 |
| | C1-305 | D | | R | M | 51.8 | 15.2 |
| | C1-306 | D | | R | R | 23.5 | 26.8 |
| | C1-307 | D | | H | K | 36.9 | 31.0 |
| | C1-308 | D | | H | M | 47.0 | 27.6 |
| | C1-309 | D | | H | R | 28.5 | 39.8 |
| | C1-310 | D | | F | K | 60.4 | 15.0 |
| | C1-311 | D | | F | M | 49.2 | 32.3 |
| | C1-312 | D | | F | R | 57.9 | 13.2 |
| | C1-313 | D | | Y | K | 51.3 | 18.5 |
| | C1-314 | D | | Y | M | 50.8 | 29.3 |
| | C1-315 | D | | Y | R | 46.1 | 17.1 |

TABLE 10

| Mutation | WT | E130 | S325 | S477 | Q481 | Content (wt %) | LA mol % |
|---|---|---|---|---|---|---|---|
| Quadruple | C1-400 | D | T | R | M | 15.8 | 15.4 |
| | C1-401 | D | T | R | K | 12.9 | 12.5 |
| | C1-334 | D | T | F | M | 1.6 | 20.8 |
| | C1-336 | D | T | G | M | 10.3 | 17.5 |

As shown in the tables 8, 9 and 10, PHA synthase mutants of the present invention were able to efficiently prepare lactate copolymers with lactyl-CoA as substrate.

INDUSTRIAL APPLICABILITY

As shown above, polyhydroxyalkanoate synthase mutants of the present invention originated from *Pseudomonas* sp. 6-19 can efficiently prepare lactate polymer and/or copolymer by using as substrate lactyl-CoA which is difficult to be used as substrate by conventional polyhydroxyalkanoate synthase.

What is claimed is:

1. A recombinant vector comprising:
   a gene encoding propionyl-CoA transferase (pct), and
   a gene encoding polyhydroxyalkanoate synthase mutant using lactyl-CoA as a substrate to produce lactate polymer or lactate copolymer,
   wherein the polyhydroxyalkanoate synthase mutant has an amino acid sequence of SEQ. ID No: 10, wherein at least the glutamine at position 481 of the amino acid sequence of SEQ. ID No: 10 is mutated.

2. The recombinant vector of claim 1, wherein at least one amino acid selected from the group consisting of glutamate at position 130; serine at position 325; and serine at position 477 in SEQ. ID No: 10 is further mutated.

3. The recombinant vector of claim 2, wherein the amino acid sequence in SEQ. ID No: 10 has any mutation of:
   a) S325T and Q481M;
   b) E130D and Q481K;
   c) S325T and Q481K;
   d) E130D and Q481M;
   e) E130D and Q481R;
   f) E130D, S325T and Q481M;
   g) E130D, S325T and Q481K;
   h) E130D, S477R and Q481K;
   i) E130D, S477R and Q481M;
   j) E130D, S477R and Q481R;
   k) E130D, S477H and Q481K;
   l) E130D, S477H and Q481M;
   m) E130D, S477H and Q481R;
   n) E130D, S477F and Q481K;
   o) E130D, S477F and Q481M;
   p) E130D, S477F and Q481R;
   q) E130D, S477Y and Q481K;
   r) E130D, S477Y and Q481M;
   s) E130D, S477Y and Q481R;
   t) E130D, S325T, S477R and Q481M;
   u) E130D, S325T, S477R and Q481K;
   v) E130D, S325T, S477F and Q481M;
   w) E130D, S325T, S477G and Q481M; or
   x) E130D, S325T, S477F and Q481K.

4. A cell or plant transformed with the recombinant vector of claim 1.

5. A cell or plant obtained from transformation with the recombinant vector of claim 1, wherein the original cell or plant does not have a gene encoding propionyl-CoA transferase.

6. A method for preparing lactate polymer or 3-hydroxyalkanoate-lactate copolymer, wherein the method comprises culturing the cell or plant of claim 5.

7. The method of claim 6, wherein the culturing is performed in a medium comprising 3-hydroxyalkanoate and the copolymer is a copolymer comprising 3-hydroxyalkanoate monomer unit and lactate monomer unit.

8. The method of claim 7, wherein the 3-hydroxyalkanoate is at least one selected from the group consisting of 3-hydroxybutyrate, 3-hydroxyvalerate, (D)-3-hydroxycarboxylic acid of the medium chain length ($C_{6-14}$), 3-hydroxypropionic acid, 3-hydroxyhexanoic acid, 3-hydroxyheptanoic acid, 3-hydroxyoctanoic acid, 3-hydroxynonanoic acid, 3-hydroxydecanoic acid, 3-hydroxyundecanoic acid, 3-hydroxydodecanoic acid, 3-hydroxytetradecanoic acid, 3-hydroxyhexadecanoic acid, 3-hydroxy-4-pentenoic acid, 3-hydroxy-4-trans-hexenoic acid, 3-hydroxy-4-cis-hexenoic acid, 3-hydroxy-5-hexenoic acid, 3-hydroxy-6-trans-octenoic acid, 3-hydroxy-6-cis-octenoic acid, 3-hydroxy-7-octenoic acid, 3-hydroxy-8-nonenoic acid, 3-hydroxy-9-decenoic acid, 3-hydroxy-5-cis-dodecenoic acid, 3-hydroxy-6-cis-dodecenoic acid, 3-hydroxy-5-cis-tetradecenoic acid, 3-hydroxy-7-cis-tetradecenoic acid, 3-hydroxy-5,8-cis-cis-tetradecenoic acid, 3-hydroxy-4-methylvaleric acid, 3-hydroxy-4-methylhexanoic acid, 3-hydroxy-5-methylhexanoic acid, 3-hydroxy-6-methylheptanoic acid, 3-hydroxy-4-methyloctanoic acid, 3-hydroxy-5-methyloctanoic acid, 3-hydroxy-6-methyloctanoic acid, 3-hydroxy-7-methyloctanoic acid, 3-hydroxy-6-methylnonanoic acid, 3-hydroxy-7-methylnonanoic acid, 3-hydroxy-8-methylnonanoic acid, 3-hydroxy-7-methyldecanoic acid, 3-hydroxy-9-methyldecanoic acid, 3-hydroxy-7-methyl-6-octenoic acid, malic acid, 3-hydroxysuccinic acid-methyl ester, 3-hydroxyadipinic acid-methyl ester, 3-hydroxysuberic acid-methyl ester, 3-hydroxyazelaic acid-methyl ester, 3-hydroxysebacic acid-methyl ester, 3-hydroxysuberic acid-ethyl ester, 3-hydroxysebacic acid-ethyl ester, 3-hydroxypimelic acid-propyl ester, 3-hydroxysebacic acid-benzyl ester, 3-hydroxy-8-acetoxyoctanoic acid, 3-hydroxy-9-acetoxynonanoic acid, phenoxy-3-hydroxybutyric acid, phenoxy-3-hydroxyvaleric acid, phenoxy-3-hydroxyheptanoic acid, phenoxy-3-hydroxyoctanoic acid, para-cyanophenoxy-3-hydroxybutyric acid, para-cyanophenoxy-3-hydroxyvaleric acid, para-cyanophenoxy-3-hydroxyhexanoic acid, para-nitrophenoxy-3-hydroxyhexanoic acid, 3-hydroxy-5-phenylvaleric acid, 3-hydroxy-5-cyclohexylbutyric acid, 3,12-dihydroxydodecanoic acid, 3,8-dihydroxy-5-cis-tetradecenoic acid, 3-hydroxy-4,5-epoxydecanoic acid, 3-hydroxy-6,7-epoxydodecanoic acid, 3-hydroxy-8,9-epoxy-5,6-cis-tetradecanoic acid, 7-cyano-3-hydroxyheptanoic acid, 9-cyano-3-hydroxynonanoic acid, 3-hydroxy-7-fluoroheptanoic acid, 3-hydroxy-9-fluorononanoic acid, 3-hydroxy-6-chlorohexanoic acid, 3-hydroxy-8-chlorooctanoic acid, 3-hydroxy-6-bromohexanoic acid, 3-hydroxy-8-bromooctanoic acid, 3-hydroxy-11-bromoundecanoic acid, 3-hydroxy-2-butenoic acid, 3-hydroxy-2-methylbutyric acid, 3-hydroxy-2-methylvaleric acid and 3-hydroxy-2,6-dimethyl-5-heptenoic acid.

* * * * *

SEQUENCE LISTING

```
<160> NUMBER OF SEQ ID NOS: 36

<210> SEQ ID NO 1
<211> LENGTH: 35
<212> TYPE: DNA
<213> ORGANISM: Artificial Sequence
<220> FEATURE:
<223> OTHER INFORMATION: Primer

<400> SEQUENCE: 1
gagagacaat caaatcatga gtaacaagag taacg                35
```

```
<210> SEQ ID NO 2
<211> LENGTH: 33
<212> TYPE: DNA
<213> ORGANISM: Artificial Sequence
<220> FEATURE:
<223> OTHER INFORMATION: Primer

<400> SEQUENCE: 2
cactcatgca agcgtcaccg ttcgtgcacg tac                                33

<210> SEQ ID NO 3
<211> LENGTH: 20
<212> TYPE: DNA
<213> ORGANISM: Artificial Sequence
<220> FEATURE:
<223> OTHER INFORMATION: Primer

<400> SEQUENCE: 3
atgcccggag ccggttcgaa                                              20

<210> SEQ ID NO 4
<211> LENGTH: 35
<212> TYPE: DNA
<213> ORGANISM: Artificial Sequence
<220> FEATURE:
<223> OTHER INFORMATION: Primer

<400> SEQUENCE: 4
cgttactctt gttactcatg atttgattgt ctctc                             35

<210> SEQ ID NO 5
<211> LENGTH: 35
<212> TYPE: DNA
<213> ORGANISM: Artificial Sequence
<220> FEATURE:
<223> OTHER INFORMATION: Primer

<400> SEQUENCE: 5
gagagacaat caaatcatga gtaacaagag taacg                             35

<210> SEQ ID NO 6
<211> LENGTH: 33
<212> TYPE: DNA
<213> ORGANISM: Artificial Sequence
<220> FEATURE:
<223> OTHER INFORMATION: Primer

<400> SEQUENCE: 6
cactcatgca agcgtcaccg ttcgtgcacg tac                                33

<210> SEQ ID NO 7
<211> LENGTH: 33
<212> TYPE: DNA
<213> ORGANISM: Artificial Sequence
<220> FEATURE:
<223> OTHER INFORMATION: Primer

<400> SEQUENCE: 7
gtacgtgcac gaacggtgac gcttgcatga gtg                                33

<210> SEQ ID NO 8
<211> LENGTH: 20
<212> TYPE: DNA
<213> ORGANISM: Artificial Sequence
<220> FEATURE:
<223> OTHER INFORMATION: Primer
```

-continued

<400> SEQUENCE: 8
aacgggaggg aacctgcagg                                                20

<210> SEQ ID NO 9
<211> LENGTH: 1677
<212> TYPE: DNA
<213> ORGANISM: Pseudomonas sp. 6-19 (KCTC 11027BP)

<400> SEQUENCE: 9

```
atgagtaaca agagtaacga tgagttgaag tatcaagcct ctgaaaacac cttggggctt      60
aatcctgtcg ttgggctgcg tggaaaggat ctactggctt ctgctcgaat ggtgcttagg     120
caggccatca agcaaccggt gcacagcgtc aaacatgtcg cgcactttgg tcttgaactc     180
aagaacgtac tgctgggtaa atccgggctg caaccgacca gcgatgaccg tcgcttcgcc     240
gatccggcct ggagccagaa cccgctctat aaacgttatt gcaaaccta cctggcgtgg      300
cgcaaggaac tccacgactg gatcgatgaa agtaacctcg cccccaagga tgtggcgcgt     360
gggcacttcg tgatcaacct catgaccgaa gcgatggcgc cgaccaacac cgcggccaac     420
ccggcggcag tcaaacgctt ttttgaaacc ggtggcaaaa gcctgctcga cggcctctcg     480
cacctggcca aggatctggt acacaacggc ggcatgccga gccaggtcaa catgggtgca     540
ttcgaggtcg gcaagagcct gggcgtgacc gaaggcgcgg tggtgtttcg caacgatgtg     600
ctggaactga tccagtacaa gccgaccacc gagcaggtat acgaacgccc gctgctggtg     660
gtgccgccgc agatcaacaa gttctacgtt tcgacctga gccgggacaa gagcctggcg      720
cggttctgcc tgcgcaacaa cgtgcaaacg ttcatcgtca gctggcgaaa tcccaccaag     780
gaacagcgag agtggggcct gtcgacctac atcgaagccc tcaaggaagc ggttgacgtc     840
gttaccgcga tcaccggcag caaagacgtg aacatgctcg gggcctgctc cggcggcatc     900
acttgcactg cgctgctggg ccattacgcg gcgattggcg aaaacaaggt caacgccctg     960
accttgctgg tgagcgtgct tgataccacc ctcgacagca cgtcgccct gttcgtcaat     1020
gaacagaccc ttgaagccgc caagcgccac tcgtaccagg ccggcgtact ggaaggccgc    1080
gacatggcga aggtcttcgc ctggatgcgc cccaacgatc tgatctggaa ctactgggtc    1140
aacaattacc tgctaggcaa cgaaccgccg gtgttcgaca tcctgttctg gaacaacgac    1200
accacacggt tgcccgcggc gttccacggc gacctgatcg aactgttcaa aaataaccca    1260
ctgattcgcc cgaatgcact ggaagtgtgc ggcaccccca tcgacctcaa gcaggtgacg    1320
gccgacatct tttccctggc cggcaccaac gaccacatca ccccgtggaa gtcctgctac    1380
aagtcggcgc aactgtttgg cggcaacgtt gaattcgtgc tgtcgagcag cgggcatatc    1440
cagagcatcc tgaacccgcc gggcaatccg aaatcgcgct acatgaccag caccgaagtg    1500
gcggaaaatg ccgatgaatg gcaagcgaat gccaccaagc atacagattc ctggtggctg    1560
cactggcagg cctggcaggc ccaacgctcg ggcgagctga aaaagtcccc gacaaaactg    1620
ggcagcaagg cgtatccggc aggtgaagcg gcgccaggca cgtacgtgca cgaacgg      1677
```

<210> SEQ ID NO 10
<211> LENGTH: 559
<212> TYPE: PRT
<213> ORGANISM: Pseudomonas sp. 6-19 (KCTC 11027BP)

<400> SEQUENCE: 10

```
Met Ser Asn Lys Ser Asn Asp Glu Leu Lys Tyr Gln Ala Ser Glu Asn
 1               5                  10                  15

Thr Leu Gly Leu Asn Pro Val Val Gly Leu Arg Gly Lys Asp Leu Leu
```

```
                20                  25                  30
Ala Ser Ala Arg Met Val Leu Arg Gln Ala Ile Lys Gln Pro Val His
            35                  40                  45

Ser Val Lys His Val Ala His Phe Gly Leu Glu Leu Lys Asn Val Leu
        50                  55                  60

Leu Gly Lys Ser Gly Leu Gln Pro Thr Ser Asp Asp Arg Arg Phe Ala
65                  70                  75                  80

Asp Pro Ala Trp Ser Gln Asn Pro Leu Tyr Lys Arg Tyr Leu Gln Thr
                85                  90                  95

Tyr Leu Ala Trp Arg Lys Glu Leu His Asp Trp Ile Asp Glu Ser Asn
            100                 105                 110

Leu Ala Pro Lys Asp Val Ala Arg Gly His Phe Val Ile Asn Leu Met
        115                 120                 125

Thr Glu Ala Met Ala Pro Thr Asn Thr Ala Ala Asn Pro Ala Ala Val
    130                 135                 140

Lys Arg Phe Phe Glu Thr Gly Gly Lys Ser Leu Leu Asp Gly Leu Ser
145                 150                 155                 160

His Leu Ala Lys Asp Leu Val His Asn Gly Gly Met Pro Ser Gln Val
                165                 170                 175

Asn Met Gly Ala Phe Glu Val Gly Lys Ser Leu Gly Val Thr Glu Gly
            180                 185                 190

Ala Val Val Phe Arg Asn Asp Val Leu Glu Leu Ile Gln Tyr Lys Pro
        195                 200                 205

Thr Thr Glu Gln Val Tyr Glu Arg Pro Leu Leu Val Val Pro Pro Gln
    210                 215                 220

Ile Asn Lys Phe Tyr Val Phe Asp Leu Ser Pro Asp Lys Ser Leu Ala
225                 230                 235                 240

Arg Phe Cys Leu Arg Asn Asn Val Gln Thr Phe Ile Val Ser Trp Arg
                245                 250                 255

Asn Pro Thr Lys Glu Gln Arg Glu Trp Gly Leu Ser Thr Tyr Ile Glu
            260                 265                 270

Ala Leu Lys Glu Ala Val Asp Val Val Thr Ala Ile Thr Gly Ser Lys
        275                 280                 285

Asp Val Asn Met Leu Gly Ala Cys Ser Gly Gly Ile Thr Cys Thr Ala
    290                 295                 300

Leu Leu Gly His Tyr Ala Ala Ile Gly Glu Asn Lys Val Asn Ala Leu
305                 310                 315                 320

Thr Leu Leu Val Ser Val Leu Asp Thr Thr Leu Asp Ser Asp Val Ala
                325                 330                 335

Leu Phe Val Asn Glu Gln Thr Leu Glu Ala Ala Lys Arg His Ser Tyr
            340                 345                 350

Gln Ala Gly Val Leu Glu Gly Arg Asp Met Ala Lys Val Phe Ala Trp
        355                 360                 365

Met Arg Pro Asn Asp Leu Ile Trp Asn Tyr Trp Val Asn Asn Tyr Leu
    370                 375                 380

Leu Gly Asn Glu Pro Pro Val Phe Asp Ile Leu Phe Trp Asn Asn Asp
385                 390                 395                 400

Thr Thr Arg Leu Pro Ala Ala Phe His Gly Asp Leu Ile Glu Leu Phe
                405                 410                 415

Lys Asn Asn Pro Leu Ile Arg Pro Asn Ala Leu Glu Val Cys Gly Thr
            420                 425                 430

Pro Ile Asp Leu Lys Gln Val Thr Ala Asp Ile Phe Ser Leu Ala Gly
        435                 440                 445
```

```
Thr Asn Asp His Ile Thr Pro Trp Lys Ser Cys Tyr Lys Ser Ala Gln
    450                 455                 460

Leu Phe Gly Gly Asn Val Glu Phe Val Leu Ser Ser Gly His Ile
465                 470                 475                 480

Gln Ser Ile Leu Asn Pro Pro Gly Asn Pro Lys Ser Arg Tyr Met Thr
                485                 490                 495

Ser Thr Glu Val Ala Glu Asn Ala Asp Glu Trp Gln Ala Asn Ala Thr
                500                 505                 510

Lys His Thr Asp Ser Trp Trp Leu His Trp Gln Ala Trp Gln Ala Gln
        515                 520                 525

Arg Ser Gly Glu Leu Lys Lys Ser Pro Thr Lys Leu Gly Ser Lys Ala
    530                 535                 540

Tyr Pro Ala Gly Glu Ala Ala Pro Gly Thr Tyr Val His Glu Arg
545                 550                 555

<210> SEQ ID NO 11
<211> LENGTH: 33
<212> TYPE: DNA
<213> ORGANISM: Artificial Sequence
<220> FEATURE:
<223> OTHER INFORMATION: Primer

<400> SEQUENCE: 11
ctgaccttgc tggtgaccgt gcttgatacc acc                              33

<210> SEQ ID NO 12
<211> LENGTH: 33
<212> TYPE: DNA
<213> ORGANISM: Artificial Sequence
<220> FEATURE:
<223> OTHER INFORMATION: Primer

<400> SEQUENCE: 12
ggtggtatca agcacggtca ccagcaaggt cag                              33

<210> SEQ ID NO 13
<211> LENGTH: 36
<212> TYPE: DNA
<213> ORGANISM: Artificial Sequence
<220> FEATURE:
<223> OTHER INFORMATION: Primer

<400> SEQUENCE: 13
cgagcagcgg gcatatcatg agcatcctga acccgc                           36

<210> SEQ ID NO 14
<211> LENGTH: 36
<212> TYPE: DNA
<213> ORGANISM: Artificial Sequence
<220> FEATURE:
<223> OTHER INFORMATION: Primer

<400> SEQUENCE: 14
gcgggttcag gatgctcatg atatgcccgc tgctcg                           36

<210> SEQ ID NO 15
<211> LENGTH: 33
<212> TYPE: DNA
<213> ORGANISM: Artificial Sequence
<220> FEATURE:
<223> OTHER INFORMATION: Primer

<400> SEQUENCE: 15
atcaacctca tgaccgatgc gatggcgccg acc                              33
```

<210> SEQ ID NO 16
<211> LENGTH: 33
<212> TYPE: DNA
<213> ORGANISM: Artificial Sequence
<220> FEATURE:
<223> OTHER INFORMATION: Primer

<400> SEQUENCE: 16
ggtcggcgcc atcgcatcgg tcatgaggtt gat                                    33

<210> SEQ ID NO 17
<211> LENGTH: 39
<212> TYPE: DNA
<213> ORGANISM: Artificial Sequence
<220> FEATURE:
<223> OTHER INFORMATION: Primer

<400> SEQUENCE: 17
ggaattcatg agaaaggttc ccattattac cgcagatga                              39

<210> SEQ ID NO 18
<211> LENGTH: 46
<212> TYPE: DNA
<213> ORGANISM: Artificial Sequence
<220> FEATURE:
<223> OTHER INFORMATION: Primer

<400> SEQUENCE: 18
gctctagatt aggacttcat ttccttcaga cccattaagc cttctg                      46

<210> SEQ ID NO 19
<211> LENGTH: 32
<212> TYPE: DNA
<213> ORGANISM: Artificial Sequence
<220> FEATURE:
<223> OTHER INFORMATION: Primer

<400> SEQUENCE: 19
aggcctgcag gcggataaca atttcacaca gg                                     32

<210> SEQ ID NO 20
<211> LENGTH: 31
<212> TYPE: DNA
<213> ORGANISM: Artificial Sequence
<220> FEATURE:
<223> OTHER INFORMATION: Primer

<400> SEQUENCE: 20
gcccatatgt ctagattagg acttcatttc c                                      31

<210> SEQ ID NO 21
<211> LENGTH: 30
<212> TYPE: DNA
<213> ORGANISM: Artificial Sequence
<220> FEATURE:
<223> OTHER INFORMATION: Primer

<400> SEQUENCE: 21
gaattcgtgc tgtcgagccg cgggcatatc                                        30

<210> SEQ ID NO 22
<211> LENGTH: 30
<212> TYPE: DNA
<213> ORGANISM: Artificial Sequence
<220> FEATURE:
<223> OTHER INFORMATION: Primer

<400> SEQUENCE: 22
gatatgcccg cggctcgaca gcacgaattc                                                30

<210> SEQ ID NO 23
<211> LENGTH: 30
<212> TYPE: DNA
<213> ORGANISM: Artificial Sequence
<220> FEATURE:
<223> OTHER INFORMATION: Primer

<400> SEQUENCE: 23
gaattcgtgc tgtcgagcca tgggcatatc                                                30

<210> SEQ ID NO 24
<211> LENGTH: 30
<212> TYPE: DNA
<213> ORGANISM: Artificial Sequence
<220> FEATURE:
<223> OTHER INFORMATION: Primer

<400> SEQUENCE: 24
gatatgccca tggctcgaca gcacgaattc                                                30

<210> SEQ ID NO 25
<211> LENGTH: 30
<212> TYPE: DNA
<213> ORGANISM: Artificial Sequence
<220> FEATURE:
<223> OTHER INFORMATION: Primer

<400> SEQUENCE: 25
gaattcgtgc tgtcgagctt tgggcatatc                                                30

<210> SEQ ID NO 26
<211> LENGTH: 30
<212> TYPE: DNA
<213> ORGANISM: Artificial Sequence
<220> FEATURE:
<223> OTHER INFORMATION: Primer

<400> SEQUENCE: 26
gatatgccca aagctcgaca gcacgaattc                                                30

<210> SEQ ID NO 27
<211> LENGTH: 30
<212> TYPE: DNA
<213> ORGANISM: Artificial Sequence
<220> FEATURE:
<223> OTHER INFORMATION: Primer

<400> SEQUENCE: 27
gaattcgtgc tgtcgagcta tgggcatatc                                                30

<210> SEQ ID NO 28
<211> LENGTH: 30
<212> TYPE: DNA
<213> ORGANISM: Artificial Sequence
<220> FEATURE:
<223> OTHER INFORMATION: Primer

<400> SEQUENCE: 28
gatatgccca tagctcgaca gcacgaattc                                                30

<210> SEQ ID NO 29
<211> LENGTH: 30

```
<212> TYPE: DNA
<213> ORGANISM: Artificial Sequence
<220> FEATURE:
<223> OTHER INFORMATION: Primer

<400> SEQUENCE: 29
gaattcgtgc tgtcgagcgg cgggcatatc                                        30

<210> SEQ ID NO 30
<211> LENGTH: 30
<212> TYPE: DNA
<213> ORGANISM: Artificial Sequence
<220> FEATURE:
<223> OTHER INFORMATION: Primer

<400> SEQUENCE: 30
gatatgcccg ccgctcgaca gcacgaattc                                        30

<210> SEQ ID NO 31
<211> LENGTH: 28
<212> TYPE: DNA
<213> ORGANISM: Artificial Sequence
<220> FEATURE:
<223> OTHER INFORMATION: Primer

<400> SEQUENCE: 31
gggcatatca aaagcatcct gaacccgc                                          28

<210> SEQ ID NO 32
<211> LENGTH: 28
<212> TYPE: DNA
<213> ORGANISM: Artificial Sequence
<220> FEATURE:
<223> OTHER INFORMATION: Primer

<400> SEQUENCE: 32
gcgggttcag gatgcttttg atatgccc                                          28

<210> SEQ ID NO 33
<211> LENGTH: 28
<212> TYPE: DNA
<213> ORGANISM: Artificial Sequence
<220> FEATURE:
<223> OTHER INFORMATION: Primer

<400> SEQUENCE: 33
gggcatatca tgagcatcct gaacccgc                                          28

<210> SEQ ID NO 34
<211> LENGTH: 28
<212> TYPE: DNA
<213> ORGANISM: Artificial Sequence
<220> FEATURE:
<223> OTHER INFORMATION: Primer

<400> SEQUENCE: 34
gcgggttcag gatgctcatg atatgccc                                          28

<210> SEQ ID NO 35
<211> LENGTH: 28
<212> TYPE: DNA
<213> ORGANISM: Artificial Sequence
<220> FEATURE:
<223> OTHER INFORMATION: Primer

<400> SEQUENCE: 35
gggcatatcc gcagcatcct gaacccgc                                          28
```

```
<210> SEQ ID NO 36
<211> LENGTH: 28
<212> TYPE: DNA
<213> ORGANISM: Artificial Sequence
<220> FEATURE:
<223> OTHER INFORMATION: Primer

<400> SEQUENCE: 36
gcgggttcag gatgctgcgg atatgccc                                      28
```